United States Patent
Lutze et al.

(10) Patent No.: US 8,292,893 B2
(45) Date of Patent: Oct. 23, 2012

(54) SURGICAL INSTRUMENT FOR TENSIONING PLATE-SHAPED ENGAGING ELEMENTS WITH RESPECT TO EACH OTHER

(75) Inventors: Theodor Lutze, Balgheim (DE); Manfred Dworschak, Duerbheim (DE); Pedro Morales, Tuttlingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 477 days.

(21) Appl. No.: 12/587,702

(22) Filed: Oct. 9, 2009

(65) Prior Publication Data

US 2010/0094362 A1 Apr. 15, 2010

Related U.S. Application Data

(63) Continuation of application No. PCT/EP2008/004129, filed on May 23, 2008.

(30) Foreign Application Priority Data

May 25, 2007 (DE) .......................... 10 2007 026 079

(51) Int. Cl.
*A61B 2/46* (2006.01)
(52) U.S. Cl. ...................................... 606/86 R; 606/99
(58) Field of Classification Search ............... 606/86 R, 606/86 A, 86 B, 99, 103, 105, 281, 139, 142, 606/205–208; 140/123, 123.5, 123.6; 24/523, 24/527
See application file for complete search history.

(56) References Cited

U.S. PATENT DOCUMENTS

2006/0064110 A1* 3/2006 Nesper et al. ................. 606/105

FOREIGN PATENT DOCUMENTS

| DE | 197 00 474 | 7/1998 |
|---|---|---|
| DE | 103 10 004 | 10/2004 |
| DE | 20 2006 007 221 | 7/2006 |

* cited by examiner

*Primary Examiner* — Kevin T Truong
*Assistant Examiner* — Diana S Jones
(74) *Attorney, Agent, or Firm* — Lipsitz & McAllister, LLC

(57) ABSTRACT

In a surgical instrument for tensioning two plate-shaped engaging elements with respect to each other at opposite sides of bone portions, a first engaging element carrying next to each other at a spacing from each other two pin-shaped or rod-shaped connecting members which pass through openings in the second engaging element, with a supporting surface for engagement on the side of the second engaging element that faces away from the first engaging element, and with a tensioning device engaging the connecting members for displacement of the connecting members and consequently of the first engaging element in the direction towards the second engaging element, to enable an individual adjustment of the engaging elements to the shape of the bone portions, it is proposed that the surgical instrument comprise next to each other two grip elements, each releasably connectable to a connecting member, and that the tensioning device engage the grip elements through a compensating element which, upon tensioning of the tensioning device, allows a differently sized displacement of the two grip elements and consequently of the two connecting members.

3 Claims, 5 Drawing Sheets

SURGICAL INSTRUMENT FOR TENSIONING PLATE-SHAPED ENGAGING ELEMENTS WITH RESPECT TO EACH OTHER

This application is a continuation of international application number PCT/EP2008/004129 filed on May 23, 2008.

The present disclosure relates to the subject matter disclosed in international application number PCT/EP2008/004129 of May 23, 2008 and German application number 10 2007 026 079.4 of May 25, 2007, which are incorporated herein by reference in their entirety and for all purposes.

BACKGROUND OF THE INVENTION

The invention relates to a surgical instrument for tensioning two plate-shaped engaging elements with respect to each other at opposite sides of bone portions, a first engaging element carrying next to each other at a spacing from each other two pin-shaped or rod-shaped connecting members which pass through openings in the second engaging element, with a supporting surface for engagement on the side of the second engaging element that faces away from the first engaging element, and with a tensioning device engaging the connecting members for displacement of the connecting members and consequently of the first engaging element in the direction towards the second engaging element.

Such an instrument is known from DE 197 00 474 and also from DE 103 10 004 B3. However, these are both configured for gripping only a single pin-shaped connecting element. An instrument is described in DE 20 2006 007 221 U1, in which the engaging elements can also be tensioned with respect to each other in an implant having two pin-shaped connecting elements arranged next to each other. To bring about the tensioning, the instrument engages a bridge which rigidly connects the two pin-shaped connecting elements to each other at their free ends. The two plate-shaped engaging elements are thereby inevitably displaced parallel to each other when the tensioning device is actuated, so that the engaging elements are unable to follow a structure of the bone plates accommodated between them, which is not exactly parallel. This results in different values of the contact pressure of the engaging elements on the bone portions lying between them and, consequently, in different tensions. Such an uneven distribution of tensions may prove unfavorable.

The object underlying the invention is to enable, in a generic instrument for tensioning engaging elements with respect to each other, which have two connecting members arranged next to each other, an adjustment of the engaging elements to different shapes and thicknesses of the bone portions lying between the engaging elements, which results in a distribution of the pressing forces which is as even as possible over the entire surface of the engaging elements.

SUMMARY OF THE INVENTION

This object is accomplished in a surgical instrument of the kind described at the outset, in accordance with the invention, in that the surgical instrument comprises next to each other two grip elements, each releasably connectable to a connecting member, and in that the tensioning device engages the grip elements through a compensating element which, upon tensioning of the tensioning device, allows a differently sized displacement of the two grip elements and consequently of the two connecting members.

Therefore, the tensioning device does not engage the grip elements directly, but rather through a compensating element which transmits the displacement movement of the tensioning device onto the two grip elements in such a way that these grip elements can execute different displacement movements. As a result, the engaging elements can adjust to the contour of the bone portions lying between them. They are not unavoidably displaced parallel to each other, but can also pivot and tilt to a slight extent with respect to each other. As a result, the pressing forces are uniformly distributed onto the bone portions over the entire area of the plate-shaped engaging elements, and there is no longer any occurrence of tension peaks.

In accordance with a preferred embodiment, it may be provided that the compensating element is configured as a carrying arm on which the grip elements are held at a spacing from each other, and on which the tensioning device engages between the holding points of the grip elements in such a way that the carrying arm is pivotable relative to the tensioning direction of the tensioning device.

In particular, it may be provided that the grip elements are held at their holding point on the carrying arm in such a way that the carrying arm is pivotable relative to the grip elements. In a manner similar to the arm of a balance, it is therefore possible for the carrying arm to transmit the displacement movement imparted to it by the tensioning device to a different extent onto the two grip elements. When the carrying arm is pivoted, the grip elements are displaced to a greater extent on one side than the carrying arm itself, and to a lesser extent on the opposite side.

The following description of preferred embodiments of the invention serves to give a more detailed explanation in conjunction with the drawings, in which:

DETAILED DESCRIPTION OF THE INVENTION

Figure 1:
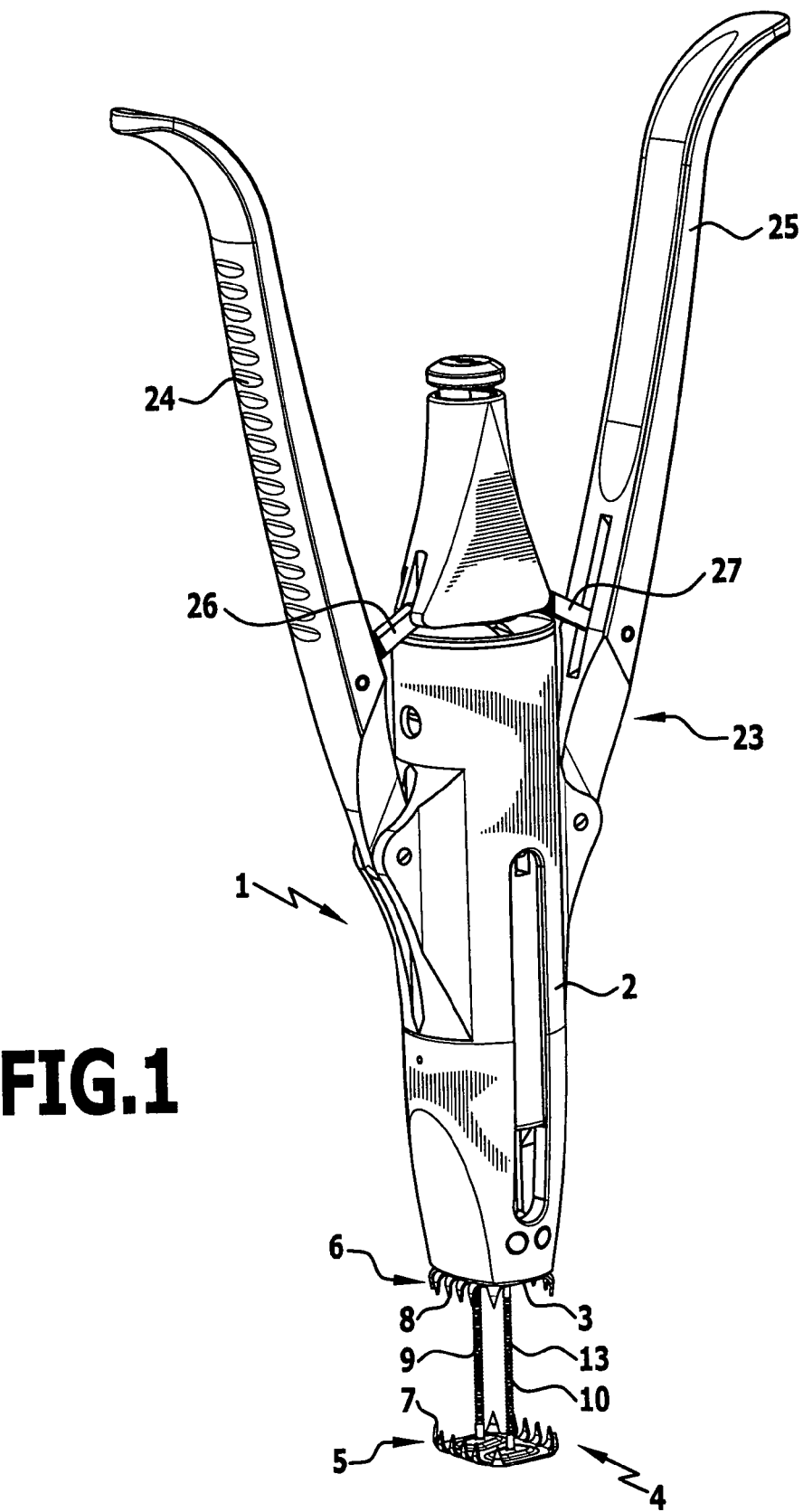
FIG. 1 shows a perspective view of a surgical instrument for tensioning two plate-shaped engaging elements with respect to each other.
Figure 2:
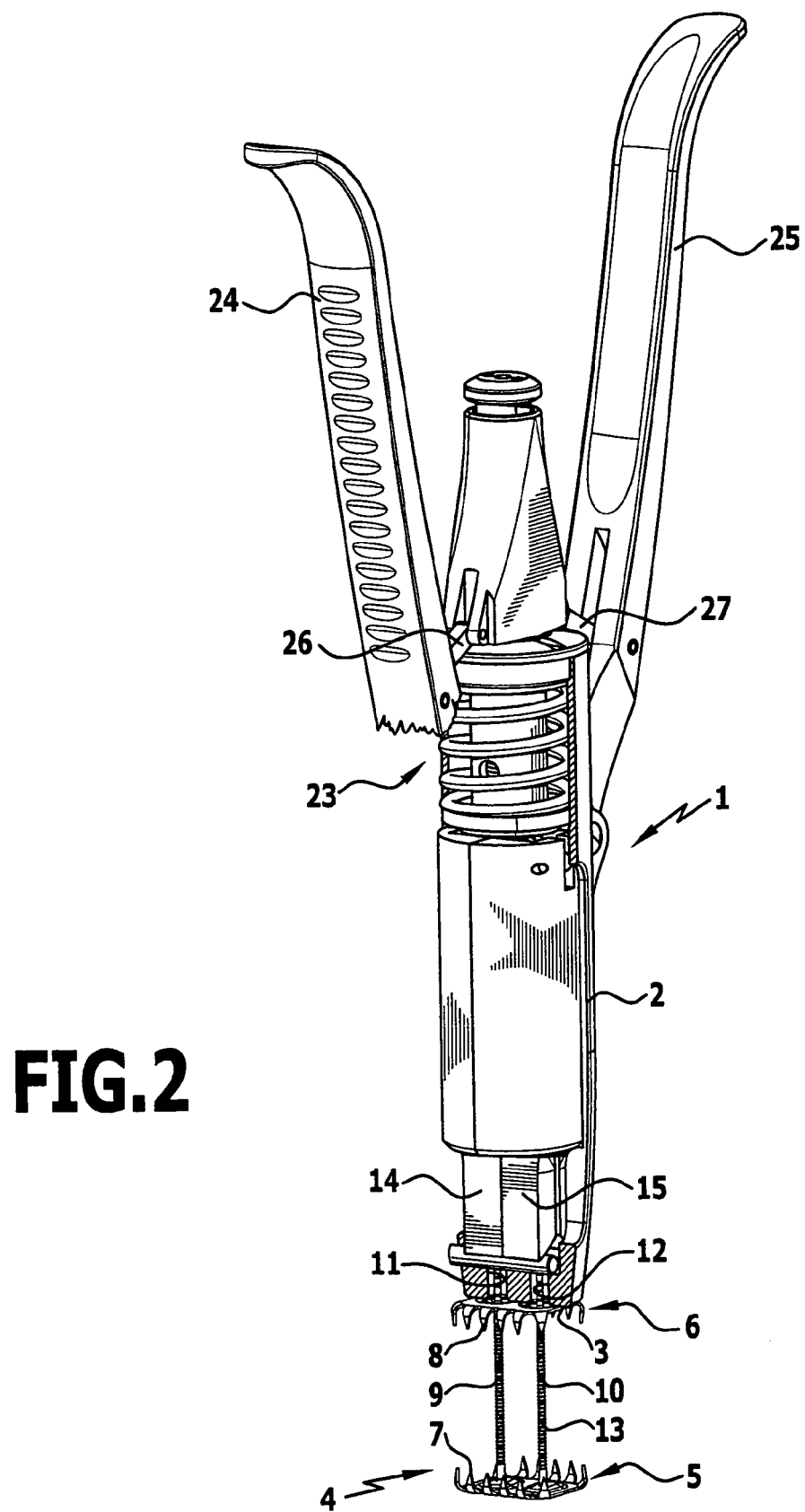
FIG. 2 shows a view similar to FIG. 1 with the housing cut open.
Figure 3:
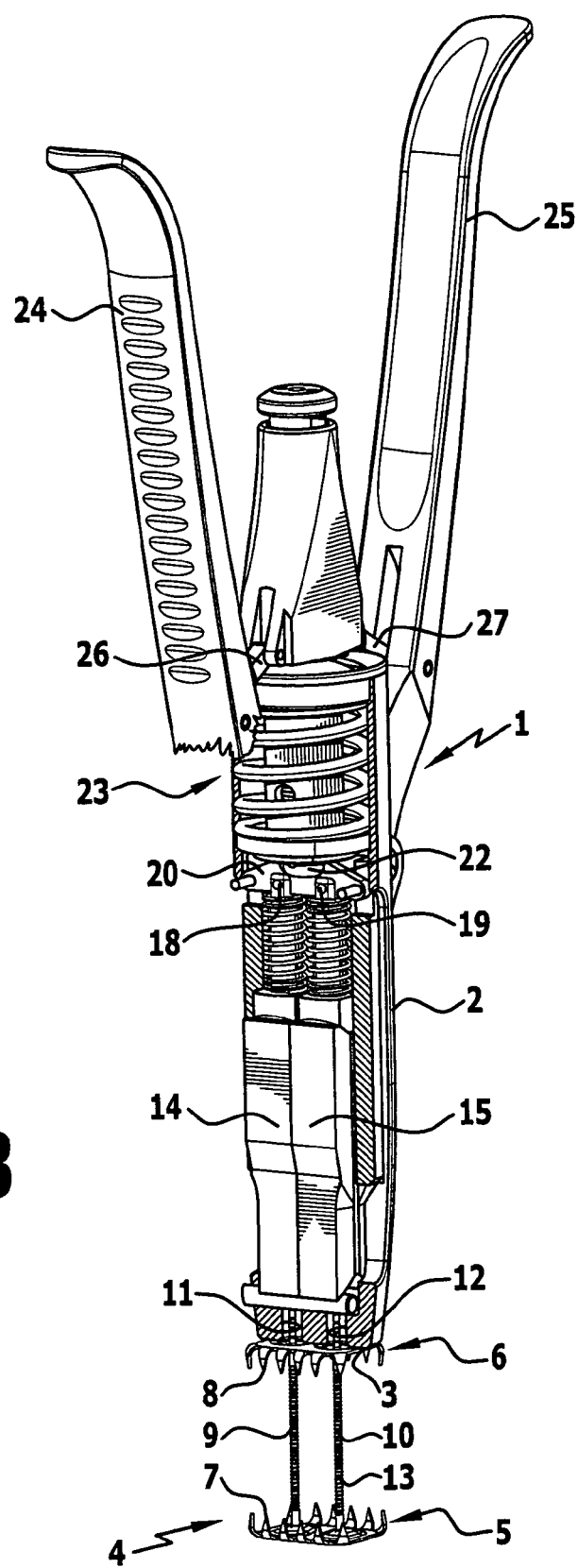
FIG. 3 shows a view similar to FIG. 2 after removal of a clamping sleeve for the grip elements.

The instrument 1 shown in the drawings is very similar in construction to the instrument described in DE 103 10 004 B3. Therefore, reference is made explicitly to the corresponding description of this previously published document. DE 103 10 004 B3 is incorporated herein and made a part hereof by reference.

This instrument 1 has a substantially cylindrical housing 2, at the bottom, distal end of which an engaging surface 3 is formed, with which the instrument 1 can be applied to an implant 4.

This implant comprises a first, lower engaging plate 5 and a second, upper engaging plate 6, which are both provided at their edge with pointed teeth 7, 8 which project from the plane of the engaging plates and point in the direction of the respective other engaging plate. The first engaging plate carries two quite long pin-shaped connecting members 9, 10 extending parallel and next to each other. The connecting members 9, 10 pass through corresponding openings in the second engaging plate 6 and extend through openings 11, 12 in the engaging surface 3 of the housing 2 into the interior of the instrument 1.

The second engaging plate 6 can be moved along the connecting members 9, 10 against the first engaging plate 5 and thereby engages in a locking manner, not shown in the drawings, in circumferential grooves 13 of the connecting members 9, 10, so that the two engaging plates can be brought closer together, but can no longer be moved apart.

Two grip elements 14, 15 of identical construction are arranged next to each other in the interior of the housing 2. Each of the two grip elements 14, 15 is associated with one of the two connecting members 9, 10 of an implant 4. The exact configuration of the grip elements is of secondary importance in conjunction with the present invention, and reference is made here to the construction according to DE 103 10 004, which corresponds substantially to the present construction.

It is essential that both grip elements 14, 15 can each engage around one of the two connecting members 9, 10 in the area of a thickening 16, 17, so that a secure tensile communication occurs between the grip elements 14, 15 and the connecting members 9, 10, i.e., upon displacing the grip elements 14, 15 along the connecting members 9, 10 tensile forces can be exerted on the connecting members 9, 10.

The two grip elements 14, 15 are each connected to a carrying arm 20, arranged in the upper part of the housing 2 and extending transversely through the housing, for pivotal movement about pivot axes 18, 19 extending parallel to each other and perpendicularly to the longitudinal axis of the connecting members 9, 10. Midway between the articulation points of the two grip elements 14, 15, the carrying arm 20 is connected to a pull member 22 of a tensioning device 23 for pivotal movement about a pivot axis 21 extending parallel to the pivot axes 18, 19. This pull member 22 can be displaced in proximal direction and thereby pulls the connecting members 9, 10 into the interior of the housing 2.

To actuate the tensioning device 23, there are mounted for pivotal movement on the outside of the housing two pivot levers 24, 25 which are located opposite each other and can displace the pull member 22 via toggle levers 26, 27. Interposed in this connection is a set of plate springs 28, which remains undeformed when low tensioning forces are exerted and is only compressed when the pulling forces generated by the pivot levers 24, 25 exceed a certain threshold value. The set of plate springs 28 thus acts as a force limiter. This construction corresponds substantially to the construction of DE 103 10 004 B3, to which explicit reference is made.

The interposition of the carrying arm 20 between the pull member 22, on the one hand, and the grip elements 14, 15, on the other hand, is of importance for the present invention because this pivotable carrying arm makes it possible for the displacement path imparted to the pull member 22 upon actuation of the tensioning device 23 to be transmitted to a different extent onto the two grip elements 14, 15.

If the carrying arm remains unpivoted, both grip elements 14, 15 are displaced in the same way. The displacement path is then identical in size to the displacement path of the pull member 22. However, if the carrying arm is pivoted during this displacement, the displacement path of the grip elements 14, 15 differs in size, the displacement path being smaller on the lowered side of the carrying arm than that of the pull member, but larger on the raised side of the carrying arm.

Figure 5:
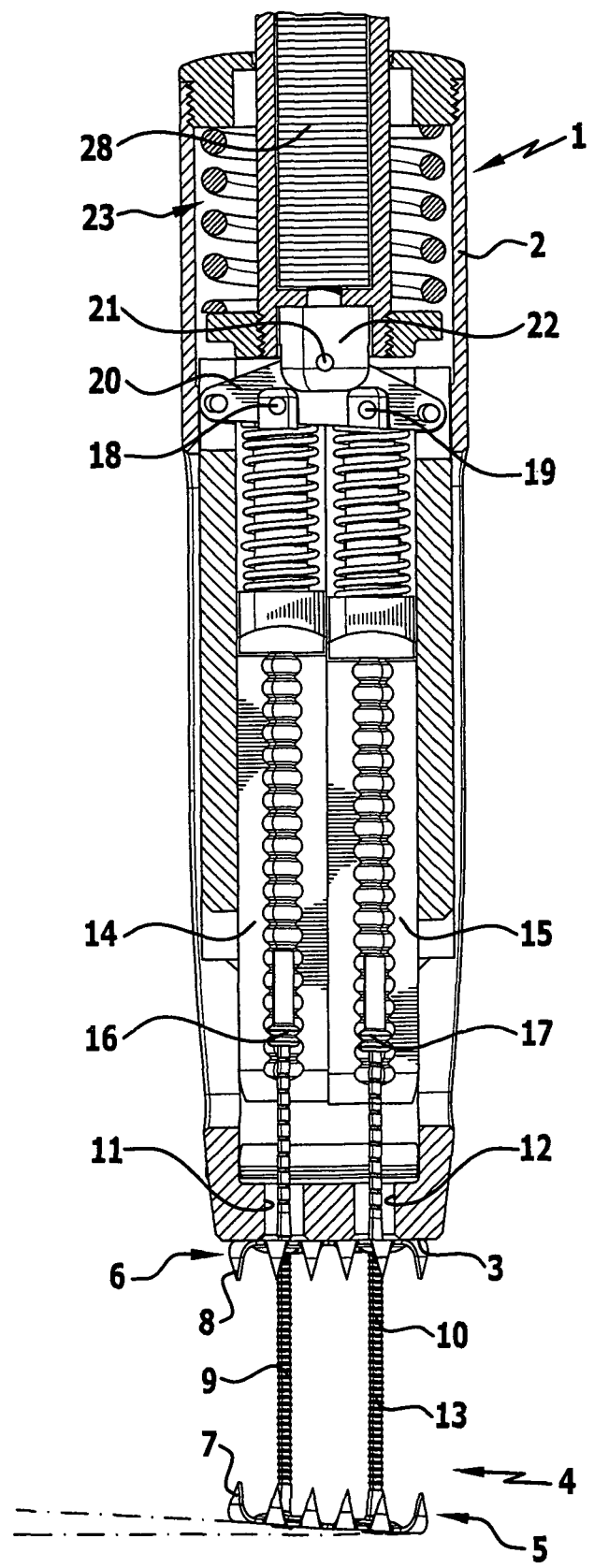
FIG. 5 shows a view similar to FIG. 4 with plate-shaped engaging elements pivoted slightly with respect to each other.

As a result, the first engaging plate 5 is also drawn nearer to the second engaging plate at one side than at the opposite side, as shown in FIG. 5, i.e., as they approach each other, the two engaging plates are inclined slightly with respect to each other, which enables them to adjust optimally to the contour of the bone portions, not shown in the drawings, lying between them.

Figure 4:
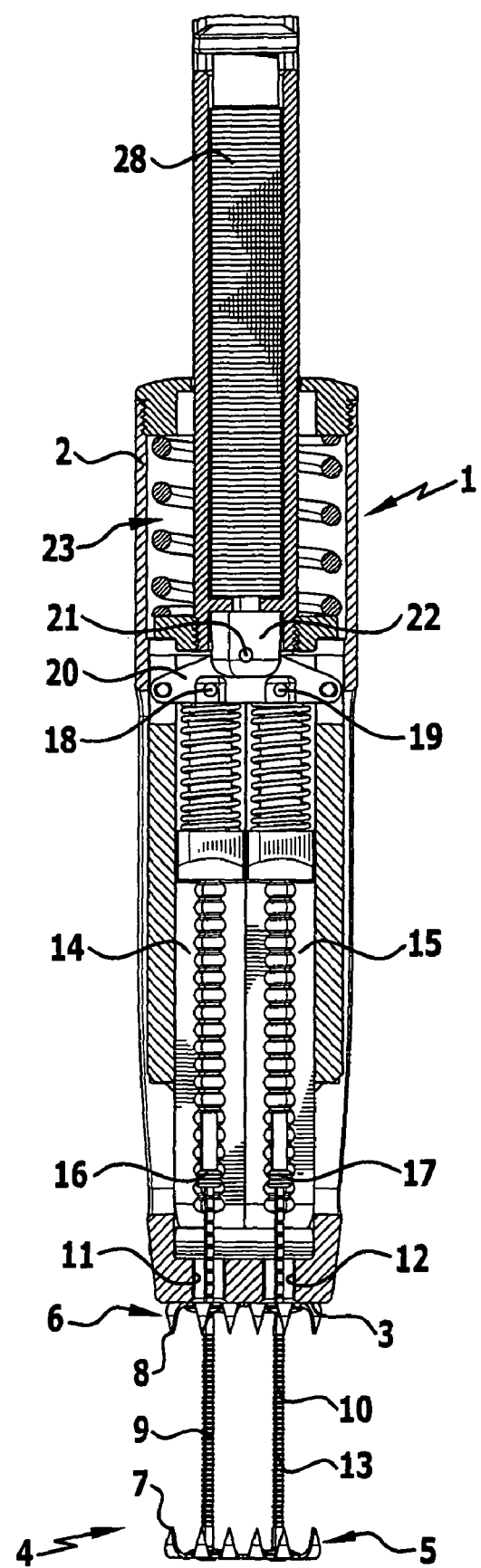
FIG. 4 shows a longitudinal sectional view through the instrument of FIGS. 1 to 3 with plate-shaped engaging elements extending parallel to each other.

If the carrying arm itself is not pivoted, the engaging plates are displaced parallel to each other during the tensioning, as shown in FIG. 4.

By providing the pivotable carrying arm, which forms a pivotable compensating bridge between the tensioning device and the two grip elements, a displacement of the engaging plates, which is adjusted to the thickness of the bone portions located between the engaging plates, is therefore possible, so that the teeth of the engaging plates along the entire circumference of the engaging plates are essentially pressed with an equally large force against the bone portions. Tension peaks can thereby be avoided.

The force limitation provided in the form of the set of plate springs 28 also ensures that the maximum forces do not exceed a certain value, which in conjunction with the pivotability of the carrying arm also contributes to the two engaging plates being able to be uniformly tensioned with respect to each other along their entire surface.

The invention claimed is:

1. Surgical instrument for tensioning first and second plate-shaped engaging elements with respect to each other at opposite sides of bone portions, the first engaging element carrying two spaced-apart pin-shaped or rod-shaped connecting members which pass through openings in the second engaging element, the surgical instrument comprising:
   a supporting surface for engagement on a side of the second engaging element that faces away from the first engaging element,
   a tensioning device engaging the connecting members for displacement of the connecting members and consequently of the first engaging element in a direction towards the second engaging element,
   two spaced-apart grip elements, each of the grip elements being releasably connectable to a respective connecting member, and
   a compensating element, the tensioning device engaging the grip elements though the compensating element, the compensating element being adapted to allow a differently sized respective displacement of each of the two grip elements and consequently of the respective two connecting members upon tensioning of the tensioning device.

2. Surgical instrument in accordance with claim 1, wherein the compensating element is configured as a carrying arm, on which the grip elements are held at a spacing from each other, and on which the tensioning device engages between holding points of the grip elements in such a way that the carrying arm is pivotable relative to a tensioning direction of the tensioning device.

3. Surgical instrument in accordance with claim 2, wherein the grip elements are held at the holding points on the carrying arm in such a way that the carrying arm is pivotable relative to the grip elements.

* * * * *